United States Patent
Batty et al.

(10) Patent No.: US 10,603,171 B2
(45) Date of Patent: *Mar. 31, 2020

(54) SURGICAL IMPLANT AND METHOD

(71) Applicant: SCIMOTANA PTY LTD, St. Kilda, Victoria (AU)

(72) Inventors: Andrew Batty, St. Kilda (AU); Paul D'Urso, St. Kilda (AU)

(73) Assignee: SCIMOTANA PTY LTD, Victoria (AU)

( * ) Notice: Subject to any disclaimer, the term of this patent is extended or adjusted under 35 U.S.C. 154(b) by 83 days.

This patent is subject to a terminal disclaimer.

(21) Appl. No.: 15/855,709

(22) Filed: Dec. 27, 2017

(65) Prior Publication Data

US 2018/0125661 A1     May 10, 2018

Related U.S. Application Data

(63) Continuation of application No. 14/001,959, filed as application No. PCT/AU2012/000199 on Feb. 28, 2012, now Pat. No. 9,883,944.

(30) Foreign Application Priority Data

Feb. 28, 2011    (AU) ................................ 2011900679

(51) Int. Cl.
    *A61F 2/28*          (2006.01)
    *A61F 2/00*          (2006.01)
    (Continued)

(52) U.S. Cl.
CPC .......... *A61F 2/2875* (2013.01); *A61F 2/0077* (2013.01); *A61F 2/28* (2013.01); *A61F 13/12* (2013.01); *A61L 31/06* (2013.01); *A61L 31/16* (2013.01); *A61B 5/686* (2013.01); *A61F 2002/009* (2013.01); *A61F 2002/3067* (2013.01); *A61F 2002/30069* (2013.01); *A61F 2002/3096* (2013.01); *A61F 2002/30672* (2013.01); *A61F 2002/30677* (2013.01); *A61F 2002/30932* (2013.01);
(Continued)

(58) Field of Classification Search
CPC .................. A61F 2/2875; A61F 2/0063; A61F 2002/009; A61F 2002/30069; A61F 2013/00259; A61F 2013/00272
See application file for complete search history.

(56) References Cited

U.S. PATENT DOCUMENTS 3,625,214 A    12/1971   Higuchi
4,938,218 A     7/1990   Goodman
(Continued)

FOREIGN PATENT DOCUMENTS

WO     2004093743 A1    11/2004
WO     2007142743 A2    12/2007

OTHER PUBLICATIONS

International Search Report, PCT/AU2012/000199, dated May 4, 2012, 2 pp.

*Primary Examiner* — Dinah Baria
(74) *Attorney, Agent, or Firm* — Volpe and Koenig, P.C.

(57) ABSTRACT

A surgical implant, which in use, provides a barrier between layers of tissue such that tissue on one side of the implant does not adhere to tissue on the other side, the improvement comprising that the implant is made of suitably anatomically shaped surgically acceptable sheet material.

15 Claims, 11 Drawing Sheets

(51) Int. Cl.
    *A61L 31/06*     (2006.01)
    *A61L 31/16*     (2006.01)
    *A61F 13/12*     (2006.01)
    *A61B 5/00*     (2006.01)
    *A61F 2/30*     (2006.01)
    *A61F 2/48*     (2006.01)

(52) U.S. Cl.
    CPC ... *A61F 2002/485* (2013.01); *A61L 2300/404* (2013.01); *A61L 2300/41* (2013.01)

(56) References Cited

U.S. PATENT DOCUMENTS

| | | |
|---|---|---|
| 5,593,441 A | 1/1997 | Lichtenstein |
| 2003/0204270 A1 | 10/2003 | Berman |
| 2005/0283256 A1 | 12/2005 | Sommerich |
| 2006/0141012 A1 | 6/2006 | Gingras |
| 2006/0167561 A1 | 7/2006 | Odar |
| 2009/0010982 A1 | 1/2009 | Abrahams |
| 2010/0166823 A1 | 7/2010 | Li |
| 2010/0233115 A1* | 9/2010 | Patel ............... A61L 15/26 424/78.08 |
| 2012/0259428 A1 | 10/2012 | Brogan |

\* cited by examiner

SURGICAL IMPLANT AND METHOD

CROSS REFERENCE TO RELATED APPLICATIONS

This application is a continuation of U.S. patent application Ser. No. 14/001,959, filed Nov. 2, 2013 as a U.S. National Phase of International Application Serial No. PCT/AU2012/000199, filed Feb. 28, 2012, which claims priority to Australian Patent Application Serial No. 2011-900679, filed Feb. 28, 2011, which are all incorporated by reference as if fully set forth.

FIELD OF INVENTION

The invention relates to the field of surgery and the provision of implants, particularly in neurosurgery.

BACKGROUND

In response to various injuries and conditions surgeons often find it necessary to separate or remove tissue from a patient. In some procedures it is desirable that tissue does not grow onto or adhere to other tissue during healing.

Decompressive craniectomy is an example of such a case. This is a neurosurgical procedure in which part of the skull is removed to allow a swelling brain room to expand. It is performed on patients that have incurred a traumatic brain injury (TBI) such as following a car accident or a fall or in patients that have suffered a stroke.

When a neurosurgeon performs a decompressive craniectomy, part of the skull is removed and either a) stored in the patient's abdomen b) stored in a bone fridge or c) discarded.

Typically for a TBI, a 10-13 cm round piece of bone is removed. The surgeon will cut along the hair line through the skin down to the bone and peel the 'skin flap' back. The surgeon will then remove bone (craniectomy) and not disturb the underlying layer of tissue, known as the dura mater.

The dura mater or dura is the outermost of the three layers of the meninges surrounding the brain and spinal cord. The other two meningeal layers are the pia mater and the arachnoid mater. The dura surrounds the brain and the spinal cord and is responsible for keeping in the cerebrospinal fluid. The bone is removed and the skin and periosteum (membrane covering the bone) is sutured back up and the patient is generally sedated in ICU to allow the brain to swell. A patient can then leave the hospital and function mindful of the area in their brain unprotected by bone.

The patient can return for surgery to restore the cranial vault in 6 weeks to 2 years. During this time, the dura will adhere and scar to the subcutaneous tissue.

To repair the cranium, the surgeon needs to re-open the same wound, and carefully separate the dura from the skin and subcutaneous tissue because the bone or implant is usually placed between these layers. This generally takes 45-60 minutes and can cause the dura to be nicked or torn.

While some surgeons improvise by using plastic bags and other ad hoc measures to minimize tissue adhesion, there are some basic flat silicone sheets, such as those by Bentec Medical, on the market which may be used.

Seprafilm® Adhesion Barrier (membrane) is an example of a basic flat sheet. This product is a sterile, bioresorbable, translucent adhesion barrier. Seprafilm Adhesion Barrier is indicated for use in patients undergoing abdominal or pelvic laparotomy as an adjunct intended to reduce the incidence, extent and severity of postoperative adhesions between the abdominal wall and the underlying viscera such as omentum, small bowel, bladder, and stomach, and between the uterus and surrounding structures such as tubes and ovaries, large bowel, and bladder.

Perthese® by Mentor is yet another example of silicone sheeting that is flexible. This is a translucent silicone elastomer sheeting material designed for medical and laboratory applications. It is made from an enhanced tear resistant elastomer that consists of dimethyl and methyl vinyl siloxane copolymers which are available as non-reinforced, reinforced and non reinforced extra firm varieties.

GORE PRECLUDE® PDX Dura Substitute is also available. This product is a flat sheet of opaque white material composed of PTFE (polytetrafluoroethylene) and is indicated for use as a temporary or permanent prosthesis for repair of dura mater during neurosurgery. GORE PRECLUDE® PDX Dura Substitute is for staged procedures and those that may require re-operation, such as, decompressive craniectomies, brain electrode mapping for seizure disorders, recurrent brain and spinal tumors.

The above references to and descriptions of prior proposals or products are not intended to be, and are not to be construed as, statements or admissions of common general knowledge in the art.

SUMMARY

According to the present invention, there is provided a temporary cranial repair barrier made from thin film sheet material that is flexible and preformed prior to use to conform to a curvature of a cranial contour, wherein in use the thin film sheet material is sufficiently flexible to enable the barrier to flex to accommodate brain swelling.

Embodiments of the barrier or implant may be for temporary or permanent use. Preferably, the implant is for temporary use.

The term "suitable anatomical shape" refers to a shape which suits the anatomy of the body where the implant is to be used. Preferably the material is curved. Even more preferably the material is shaped to conform to a region of the human cranium. More preferably the material is shaped to conform to the temporo-parietal or frontal lobe of the cranium. Preferably the pre-contoured material is suitable for left and right sides of the frontal lobe (bi-frontal) or suitable for the temporo-parietal lobe. Conveniently the pre-contoured material for the left or right side of the frontal lobe is adjustable for the left or right side by inverting the material from one side to the other. More preferably the surgical implant is oversized enabling the surgeon to trim it to suit the required size of the cranial defect.

The term "surgically acceptable sheet material" refers to implant material that is biologically inert relatively thin material such as sheet material in the form of silicone, polytetrafluoroethylene or other materials with the desirable properties. The sheet material may include a matrix, mesh, gauze and the like. The sheet material may also be transparent or opaque. The material may be biodegradable and/or resorbable.

Preferably the sheet material is thin and flexible. More preferably the sheet material is around 0.5 mm thick and is made of pre-shaped medical grade silicone film. It is preferred particularly that the sheet material is less than 0.5 mm thick.

Optionally the sheet material is reinforced In certain areas to assist in suture retention; the reinforcement including increasing the material thickness or adding a second, more resilient material, such as woven polyester. Additionally the surgical implant may contain fixation sites, such as perforations, with or without reinforcement, that allow sutures screws or rivets to be used to secure the implant to the surrounding hard or soft tissues. Preferably the sheet material includes one or more areas of reinforcement adapted to prevent sutures from pulling out or cutting through the sheet.

Optionally the sheet material may have other useful properties. For example the sheet material may incorporate one or more pharmaceutical compositions, such as antibiotics and anti inflammatory compounds. Such agents may be introduced via material porosity or via the incorporation of a second material with such porosity that may or may not be biodegradable at a predetermined rate.

In a preferred form, embodiments of the present invention are pre-shaped and pre-contoured to allow the implant to conform to the anatomy of the cranium. Other advantages include that the implant is thin and flexible and or elastic, allowing the brain to continue to swell after initial surgery. Further, the implant is modifiable which means that it can be trimmed intra-operatively. The implant may be permanent so that it will not resorb or be semi-permanent or slowly resorbable so re-implantation of the bone or another implant can be carried out at the best time to promote patient recovery.

Other embodiments of the invention relate to a surgical method of providing a barrier between layers of tissue by use of an implant such that tissue on one side of the implant does not adhere to tissue on the other side, the improvement comprising appropriately inserting into a patient the implant wherein the implant is made of surgically acceptable sheet material and is provided pre-shaped and pre-contoured into a suitable anatomical shape.

Preferably the implant used is that according to embodiments of the invention in a decompressive craniectomy or when a second stage cranioplastic procedure is likely to be necessary In another embodiment, the invention provides an implant made of surgically acceptable biocompatible sheet material incorporating monitoring probes. Such probes may be incorporated into the invention at the time of manufacture or be attached to specially designed fixtures that allow such probes to be held in position such that they may be secured in direct contact with the underlying brain or associated structures by way of apertures within the implant. Such probes may have one or numerous monitoring functions such as intracranial pressure, temperature, electroencephalometric, blood gas saturation, pH, and microdialysis for biochemical monitoring.

In yet another embodiment, the invention provides an implant made of surgically acceptable sheet material incorporating therapeutic delivery mechanisms or substances. Such mechanisms or substances may be incorporated into the implant at the time of manufacture by direct binding via porosity of the material or be bound to an incorporated delivery material. Alternatively, the mechanisms or substances may be attached to specially designed fixtures that allow such probes to be held in position such that they may be secured in direct contact with the underlying brain or associated structures by way of apertures within the implant. Such a mechanism may incorporate enclosed channels within the implant to deliver therapeutic substances to the brain and associated tissues via apertures or probes. Such substances may include antibiotic, anticonvulsant, stem cells or drugs that limit secondary neuronal damage. Such a mechanism may Include slow release biodegradable substances that release therapeutic agents in a predictable time released way.

Another embodiment of the invention relates to the provision of an implant made of surgically acceptable sheet material with an enclosed system of channels that allow the circulation of fluid to and from an external device incorporating a positive or negative pressure hydraulic pump. For example such a system could allow the circulation of fluid to modify the temperature of the brain. Such a system could induce regional hypothermia of the brain.

Yet another embodiment of the invention relates to the provision of an implant made of surgically acceptable sheet material with a network of channels that allow the closed circulation of fluid to and from an external device incorporating a positive or negative pressure hydraulic pump. A semi-permeable membrane may be used between such channels and the surface of the brain. The membrane may be designed so that only substances with specific molecular weights may cross.

This would allow osmotic forces to be harnessed and allow substance or fluids to cross selectively to or from the brain for therapeutic purposes.

Still another embodiment of the invention relates to the provision of an implant made of surgically acceptable sheet material with porosity or a scaffold and a network of channels to and from an incorporated port or reservoir. Such a port could be accessed percutaneously via injection or through access apertures so that therapeutic substances and stem cells could be introduced to promote the formation of new bone to integrate the invention with the surrounding skull.

In all of these aspects of the invention, the implant is provided pre-shaped and pre-contoured into a suitable anatomical shape.

Although described primarily in relation to the human cranium, embodiments of the implant of the present invention may be suitably shaped and fabricated so that it may be used elsewhere in the body including but not limited to the treatment of conditions of the chest, abdomen, pelvis and limbs.

DETAILED DESCRIPTION OF ILLUSTRATIVE EMBODIMENT OF THE INVENTION

The invention will now be described with reference to the following non limiting illustration.

Figure 1:
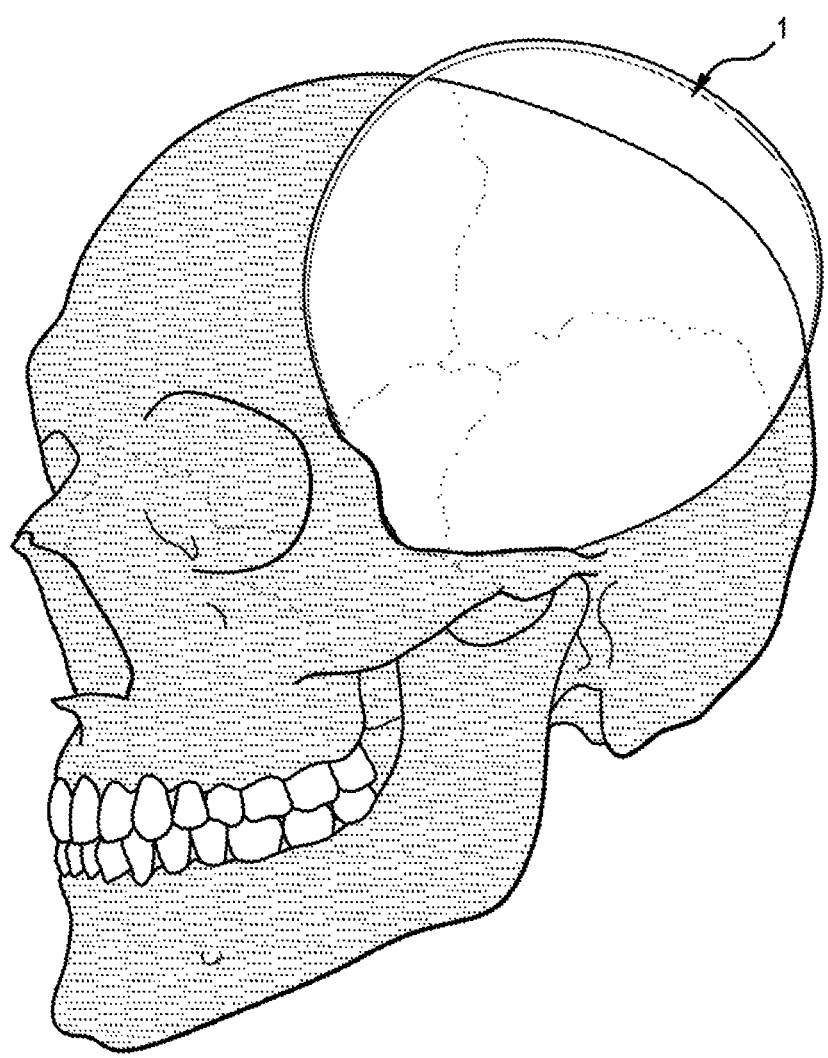
FIG. 1 is a representation of implants suitable for procedures on the temporo-parietal lobe of a human cranium.
Figure 2:
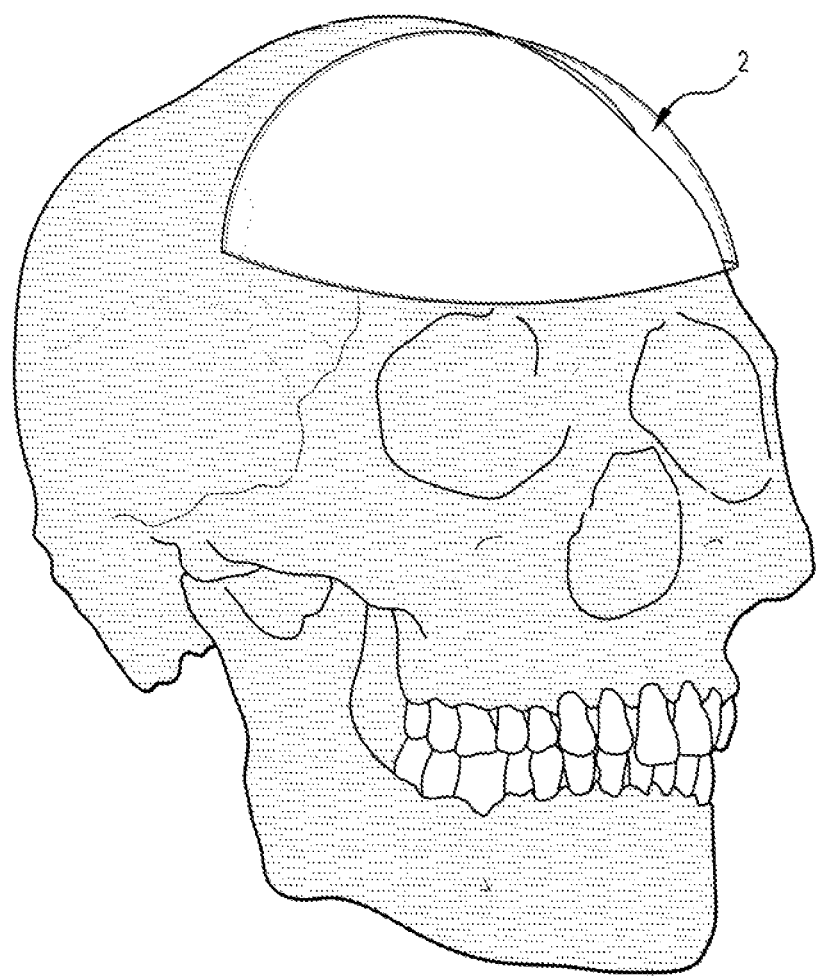
FIG. 2 is a representation of an implant suitable for procedures on the frontal lobe of a human cranium.

FIGS. 1 and 2 show implants 1, 2 suitable for temporo-parietal and frontal lobe use on a skull, respectively. The surgeon uses standard surgical techniques to fit the implant however it should be noted that compared to using a flat sheet the pre-shaped and pre-contoured implant of the present invention is simpler to fit, saves operating theatre time and minimizes discomfort as a flat sheet may buckle or overlap. Further, the curved nature of the implant of the present invention means that it is more likely to remain in place in the defect. A flat sheet may buckle or overlap and cause discomfort and make a second procedure necessary. As can be seen, the example implants are three dimensional concave structures configured to conform to a temporo-parietal lobe and a frontal lobe of a cranium, respectively, without kinks or overlap.

Figure 3:
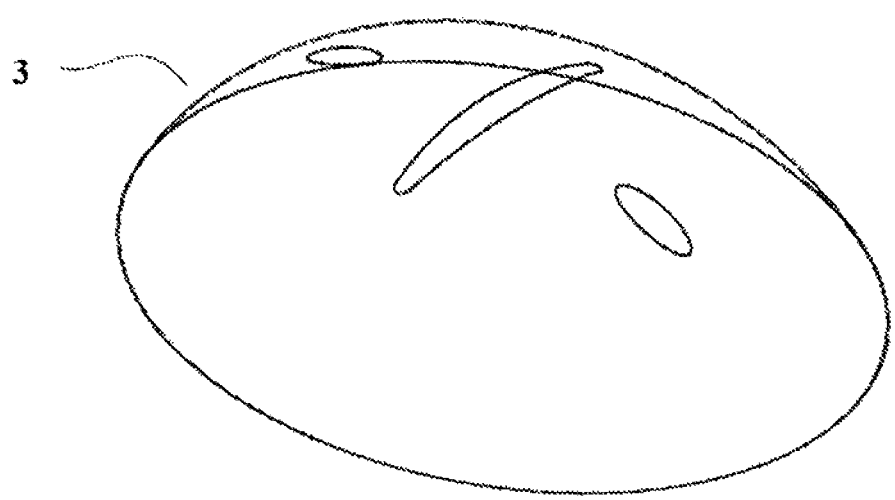
FIG. 3 is a representation of an implant according to an embodiment of the present disclosure.

FIG. 3 shows an implant 3 consistent with disclosed embodiments.

Figure 4:
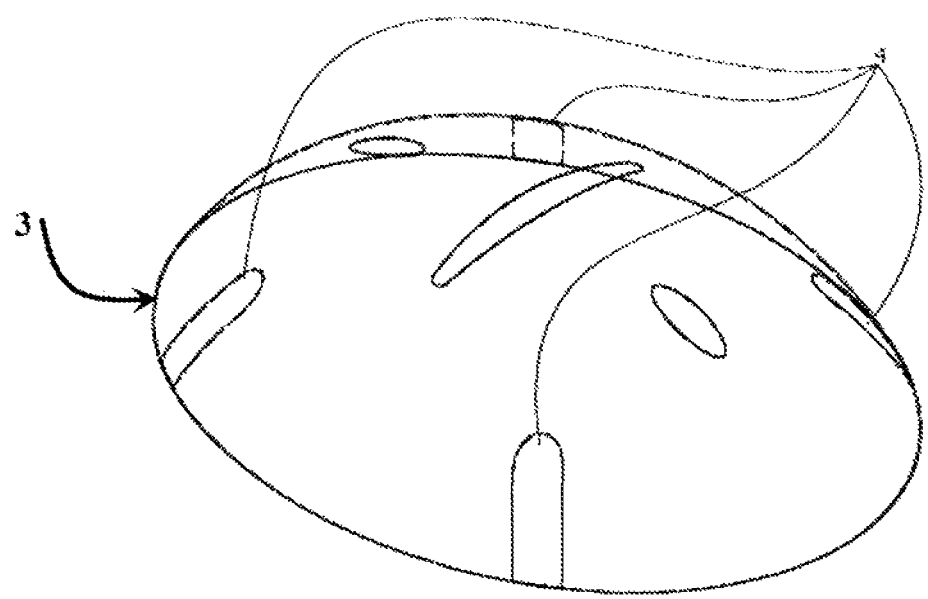
FIG. 4 is a representation of an implant including reinforcement in peripheral areas and/or fixation sites.

FIG. 4 shows an embodiment of implant 3 that includes a plurality of areas 4. Areas 4 may be reinforcement areas and/or fixation sites.

Figure 5:
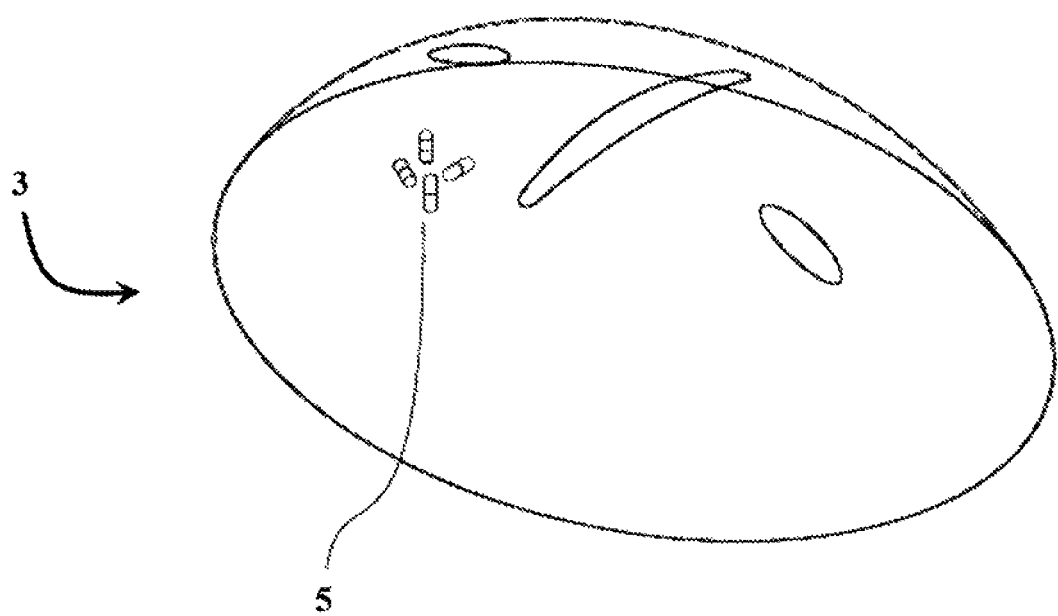
FIG. 5 is a representation of an implant incorporating pharmaceutical compositions.

FIG. 5 shows that implant 3 may incorporate one or more pharmaceutical compositions 5, such as antibiotics and anti-inflammatory compounds. Such agents may be introduced via material porosity or via the incorporation of a second material with such porosity that may or may not be biodegradable at a predetermined rate.

Figure 6:
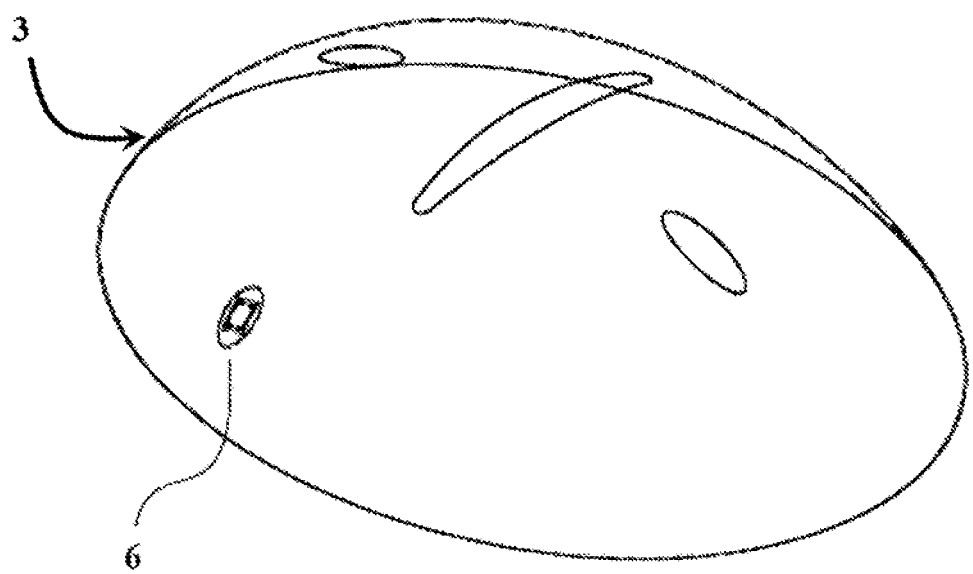
FIG. 6 is a representation of an implant including a monitoring probe.

FIG. 6 shows an embodiment of implant 3 that includes a monitoring probe 6. Monitoring probe 6 may be incorporated into implant 3 at the time of manufacture or be attached to specially designed fixtures that allow probe 6 to be held in position such that probe 6 may be secured in direct contact with the underlying brain or associated structures by way of apertures within implant 3. Probe 6 may have one or numerous monitoring functions such as intracranial pressure, temperature, electroencephalometric, blood gas saturation, pH, and microdialysis for biochemical monitoring.

Figure 7:
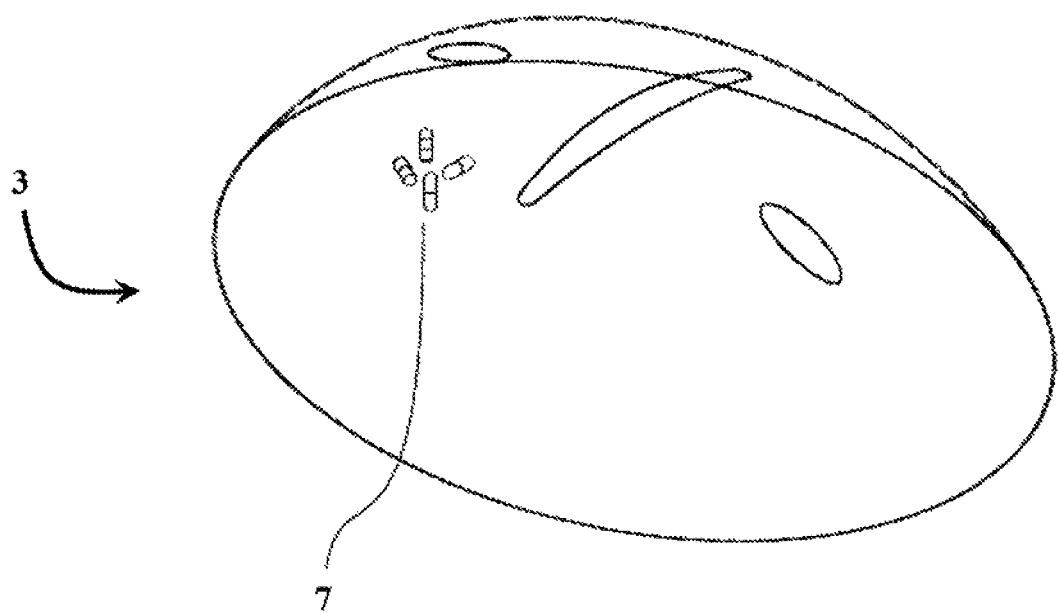
FIG. 7 is a representation of an implant incorporating slow release biodegradable substances.

FIG. 7 shows an embodiment of implant 3 that includes a therapeutic delivery mechanism or substance, such as slow release biodegradable substances 7 that release therapeutic agents in a predictable time released way.

Figure 8:
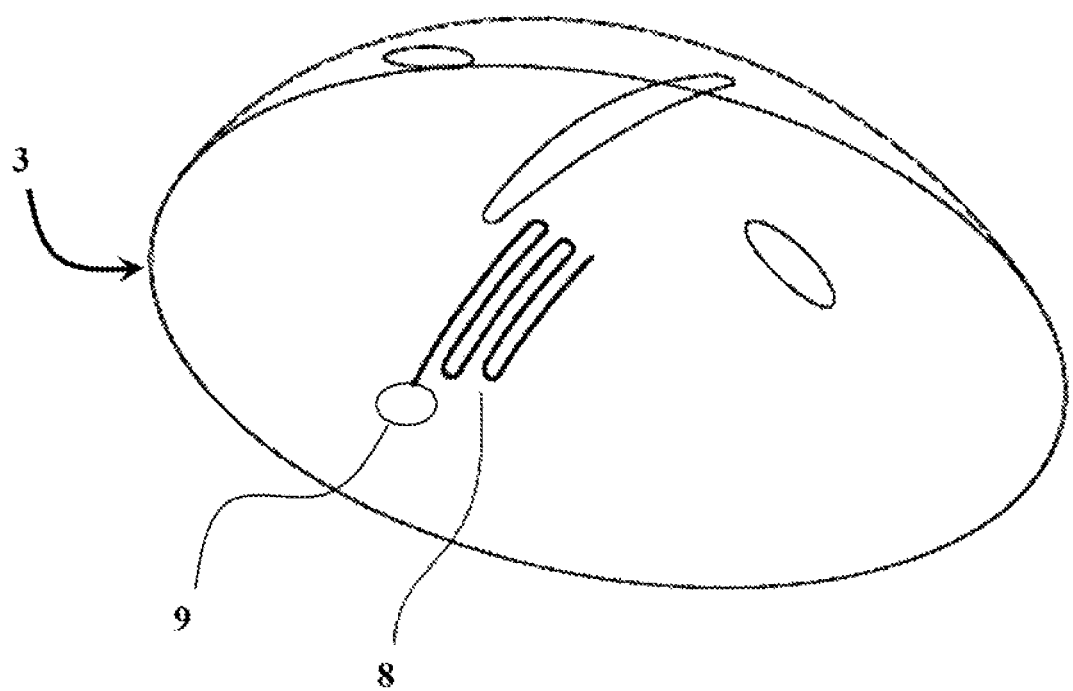
FIG. 8 is a representation of an implant including an enclosed channel accessible via apertures or probes.

FIG. 8 shows an embodiment of implant 3 that includes an enclosed channel 8 which is accessible via a mechanism 9. Mechanism 9 may be an aperture and/or probe.

Figure 9:
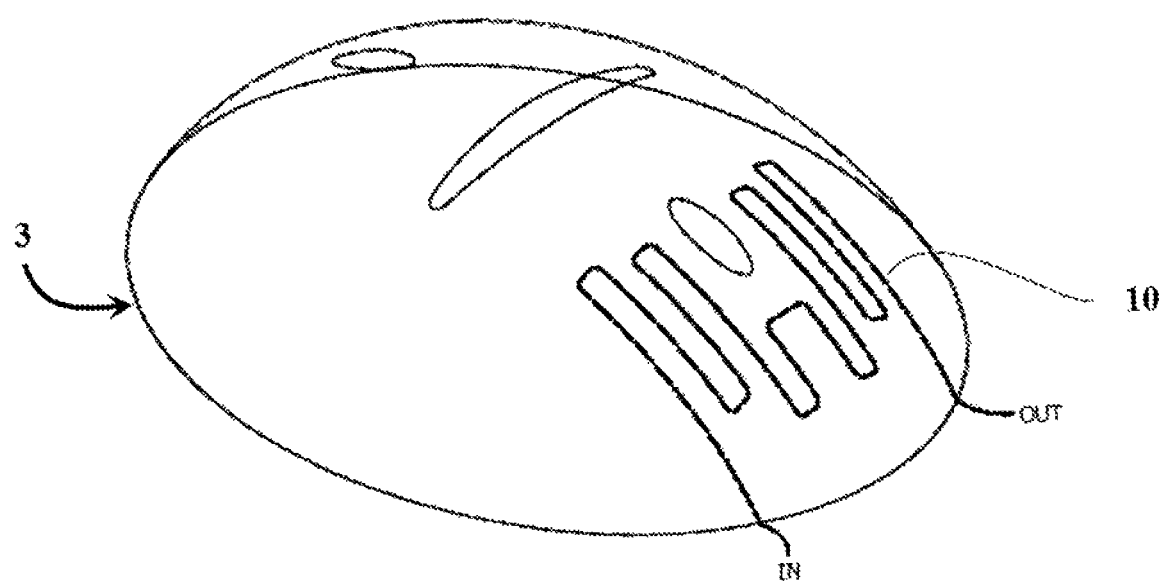
FIG. 9 is a representation of an implant including a network of channels allowing closed circulation of fluid.

FIG. 9 shows an embodiment of implant 3 that includes a network of channels 10. The network of channels 10 may allow closed circulation of fluid to and from an external pump.

Figure 10A:
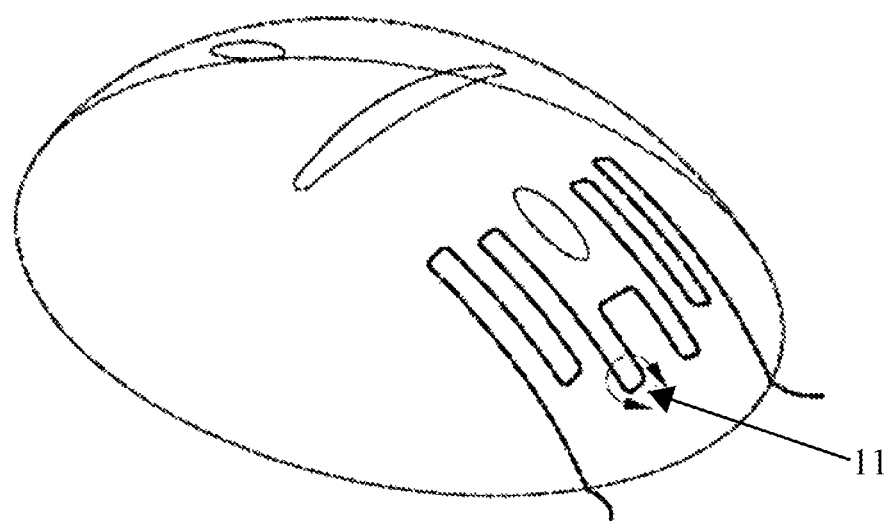
FIG. 10A is a representation of an implant including a semi-permeable membrane.
Figure 10B:
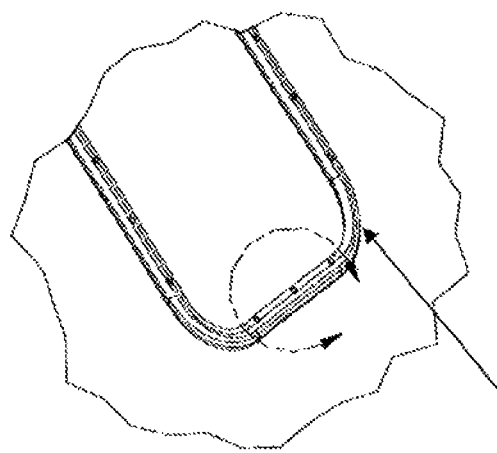
FIG. 10B is an enlarged view of the encircled portion of the implant illustrated in FIG. 10A.
Figure 10C:
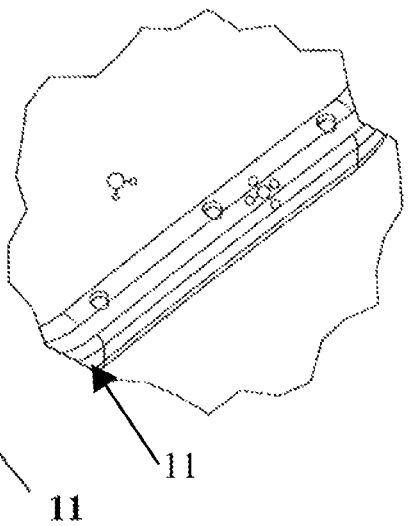
FIG. 10C is an enlarged view of the encircled portion of the portion of the implant illustrated in FIG. 10B.

FIGS. 10A-C show an embodiment of implant 3 that includes a semi-permeable membrane 11. The semi-permeable membrane 11 may be used between channels 10 and the surface of a brain. The membrane may be designed so that only substances with specific molecular weights may cross. The detail view of semi-permeable membrane 11 depicted in FIG. 10B show an example construction that includes successive layers of material. The enlarged detail view in FIG. 10C shows how pores of various size, shape, position, molecular composition, material composition, polarity or other differences may be integrated in the successive layers of membrane material to achieve permeability of specific molecular weights.

Figure 11:
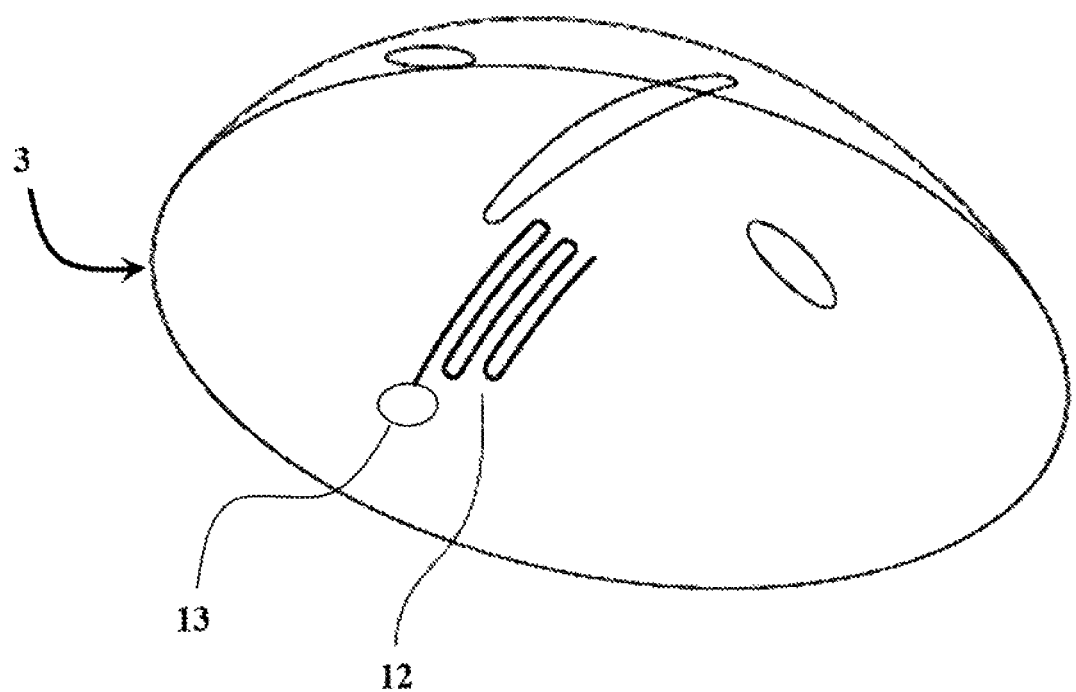
FIG. 11 is a representation of an implant including a network of channels to and from an incorporated port or reservoir.

FIG. 11 shows an embodiment of implant 3 that includes a network of channels 12. The network of channels 12 may be connected to and from an incorporated port or reservoir 13. Such a port could be accessed percutaneously via injection or through access apertures so that therapeutic substances and stem cells could be introduced to promote the formation of new bone to integrate the invention with the surrounding skull.

Throughout this specification and the claims that follow, unless the context requires otherwise the words "comprise", "comprises", "comprising" will be understood to mean the inclusion of the stated Integer, step or group of integers or steps but not the exclusion of any of other integer, step or group of integers or steps.

What is claimed it:

1. A surgical implant consisting essentially of a thin sheet of biologically inert material;
   wherein said implant is elastic,
   wherein said implant is a pre-shaped three dimensional concave structure so as to conform to a region of a human cranium without kinks or overlap such that, in use, the pre-shaped three dimensional concave structure assists the implant to remain in place in a cranial defect;
   wherein the biologically inert material is one of a medical grade flexible silicone film or a medical grade flexible PTFE film;
   wherein, in use, the implant is non-adherent to tissue and provides a barrier between layers of tissue that contact respective sides of the implant such that tissue on one side of the implant does not adhere to tissue on an opposite side of the implant, and
   wherein, in use, the implant flexes to accommodate a swelling brain.

2. A surgical implant according to claim 1, wherein the implant has a thickness of less than 0.5 mm.

3. A surgical implant according to claim 1, wherein the region of a human cranium is a temporo-parietal or frontal lobe.

4. A surgical implant according to claim 1, wherein the implant is reinforced in peripheral areas for suture retention, or the implant contains fixation sites that allow sutures screws or rivets to be used to secure the implant to surrounding hard or soft tissues.

5. A surgical implant according to claim 1, wherein the implant incorporates one or more pharmaceutical compositions.

6. A surgical implant according to claim 5, wherein the one or more pharmaceutical compositions include antibiotics or anti-inflammatory compounds.

7. A surgical implant according to claim 1, wherein the implant incorporates monitoring probes.

8. A surgical implant according to claim 7, wherein the monitoring probes have one or numerous monitoring functions selected from intracranial pressure, temperature, electroencephalometric, blood gas saturation, pH and microdialysis for biochemical monitoring.

9. A surgical implant according to claim 1, wherein the implant comprises therapeutic substances that are time releasable.

10. A surgical implant according to claim 1, wherein the implant further includes enclosed channels accessible via apertures or probes configured to deliver therapeutic substances to the brain and associated tissues.

11. A surgical implant according to claim 1, wherein the implant further includes a network of channels that allow closed circulation of fluid to and from an external device incorporating a positive or negative pressure pump.

12. A surgical implant according to claim 11, further including a semi-permeable membrane for communication of fluid between the channels and a surface of a brain.

13. A surgical implant according to claim 1, wherein the sheet comprises a network of channels and a reservoir in communication therewith.

14. A surgical implant according to claim 1, wherein the sheet comprises a network of channels and an incorporated port in communication therewith such that the port is accessible percutaneously via injection or through access apertures when the implant is implanted in a cranium, therapeutic substances and stem cells can be introduced to promote the formation of new bone to integrate the implant.

15. A surgical method including the steps of:
(a) providing an implant according to claim 1; and
(b) fitting the implant to the temporo-parietal or frontal lobe of a cranium.

\* \* \* \* \*